United States Patent [19]

Pigerol et al.

[11] 4,108,865
[45] Aug. 22, 1978

[54] THIOPHENE COMPOUNDS AND THE PRODUCTION THEREOF

[75] Inventors: Charles Pigerol, Saint-Ouen; Paul de Cointet de Fillain, Sisteron; Claude Grain, Volonne; Jacques Le Blay, Luisant, all of France

[73] Assignee: Labaz, Paris, France

[21] Appl. No.: 662,927

[22] Filed: Mar. 1, 1976

Related U.S. Application Data

[63] Continuation of Ser. No. 501,854, Aug. 29, 1974, abandoned.

[51] Int. Cl.² ............... C07D 333/00; A01N 9/00
[52] U.S. Cl. ........................... 260/329 R; 424/275
[58] Field of Search ............... 260/329 R, 332.2 A

[56] References Cited

U.S. PATENT DOCUMENTS 3,755,412  8/1973  Taranko et al. ............... 260/332.2

Primary Examiner—A. Siegel
Attorney, Agent, or Firm—Mason, Kolehmainen, Rathburn & Wyss

[57] ABSTRACT

Thiophene compounds of formula:

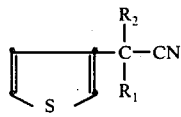

I wherein $R_1$ represents an alkyl radical containing 1 to 4 carbon atoms, a cycloalkyl, cycloalkenyl or aralkyl radical, $R_2$ represents an atom of hydrogen or a methyl radical with the proviso that when $R_2$ represents methyl $R_1$ represents alkyl, or $R_1$ and $R_2$, when they are taken together, represent, with the carbon atom to which they are attached, a cyclopolymethylene radical having from 3 to 6 carbon atoms, whereby a reaction medium comprising a solvent and a compound of the general formula:

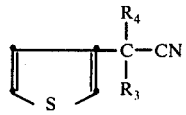

II wherein $R_3$ represents an atom of alkali metal, and $R_4$ represents an atom of hydrogen or of alkali metal is treated at a temperature between $-20°$ and $+80°$ C with the appropriate quantity of a halide of the general formula:

$$R_5X \qquad \text{III}$$

in which X represents an atom of fluorine, chlorine, bromine, or iodine and $R_5$ represents an alkyl radical containing 1 to 4 carbon atoms, a cycloalkyl, cycloalkenyl or aralkyl radical or the group $-CH_2(CH_2)_nX$ in which $n$ is an integer in the range of from 1 to 4 inclusive and X has the meaning given above with the proviso that when $R_4$ represents methyl $R_5$ represents alkyl, and when $R_3$ and $R_4$ both represent an atom of alkali metal $R_5$ represents the group $-CH_2(CH_2)_nX$ to obtain the desired thiophene derivative of formula I.

The derivatives of formula I are useful as intermediate products for preparing pharmacologically active compounds.

1 Claim, No Drawings

THIOPHENE COMPOUNDS AND THE PRODUCTION THEREOF

This is a continuation of application Ser. No. 501,854 filed Aug. 29, 1974, now abandoned.

This invention relates to a process for preparing thiophene derivatives as well as to the derivatives produced thereby.

A first object of the invention is to provide a process for the preparation of thiophene derivatives corresponding to the general formula:

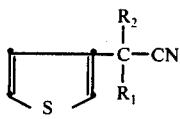 I wherein $R_1$ represents an alkyl radical containing 1 to 4 carbon atoms, a cycloalkyl, cycloalkenyl or aralkyl radical, $R_2$ represents an atom of hydrogen or a methyl radical with the proviso that when $R_2$ represents methyl $R_1$ represents alkyl, or $R_1$ and $R_2$, when they are taken together, represent, with the carbon atom to which they are attached, a cyclopolymethylene radical having from 3 to 6 carbon atoms.

Another object of the invention is concerned with the derivatives obtained by means of the process of the invention as well as with the new thiophene derivatives corresponding to the general formula:

 Ia wherein $R_1$ represents a cyclohexyl or benzyl radical.

When $R_1$ and $R_2$ are different or do not form a polymethylene radical, the compounds of formula I exist in the form of optical isomers or racemic mixtures. The new derivatives corresponding to formula Ia above in the form of either racemates or optical isomers are also included within the scope of the present invention. Amongst the nitriles of formula Ia, the following may be cited more particularly:

alpha-(3-thienyl)-alpha-cyclohexyl-acetonitrile which is the preferred compound of the invention.

The nitriles of formula I, when they are mono-substituted in alpha, enable in their turn the corresponding alpha-mono-substituted (3-thienyl)-acetic acids to be prepared easily and with good yield since it is merely necessary to hydrolyze them by means, for example, of a hydroalcoholic solution of potassium hydroxide. These alpha-mono-substituted nitriles may also be hydrolyzed by means, for example, of hydrogen peroxide in an alkaline medium to obtain the corresponding amide which may then be hydrolyzed by means, for example, of a glycolic solution of potassium hydroxide to provide the corresponding acids after acidification of the salts so formed.

Some alpha-mono-substituted (3-thienyl)-acetic acids are already known as extremely useful intermediate compounds for the preparation of thiophene derivatives presenting valuable pharmacological properties.

These thiophene derivatives are more particularly (3-thienyl)-acetic esters mono-substituted in the alpha position.

A class of such (3-thienyl)-acetic esters has been published and described in French BSM No. 5504 M as being capable of treating spasmodic and painful states of the digestive, biliary and urinary tracts, of the arteriovenous system and of the pelvic organs.

One of the best known compounds of that series is gamma-N-hexamethylene-iminoethyl ester of 2-cyclohexyl-3-thienyl-acetic acid of which the generic name is cetiedyl.

Cetiedyl has proved to be very useful as an antiischemia and periheral vasoregulator and may be considered as being presently the most effective agent for the treatment of peripheral arterial diseases [Lille Medical Actualites, 3eme Serie, Tome XVIII, pp. 1303–1312 (1973)].

However, the processes known up to present for the preparation of the starting alpha-mono-substituted (3-thienyl)-acetic acids in question are far from satisfactory when applied on the industrial scale.

These processes are generally relatively complicated and involve in particular reactions which must be maintained at very low temperatures, usually below $-50°$ C, by means of reagents which are both costly and difficult to obtain through ordinary trade channels. Furthermore, to obtain the end-product a fairly large number of intermediary stages must be gone through counting from the commercially available starting-thiophene. In addition, certain intermediary steps must be performed by means of a reaction involving the use of organo-metallic derivatives, which is of course a very delicate reaction to carry out on the industrial scale since it requires the use of anhydrous ethers which are generally very volatile. These methods are also most unrewarding if account is taken of the care and effort which must go into their use. In view of this disadvantage and of those listed above, the processes so far known can only be suitable for laboratory work and could not be usefully applied on the industrial scale.

Since, as indicated above, the alpha-mono-substituted nitriles prepared in accordance with the process forming one of the objects of the invention may be easily converted to the corresponding alpha-mono-substituted (3-thienyl)-acetic acids, it follows that if the process forming one of the objects of the invention and which provides the nitriles in question offers advantages as compared with what is known up to present, this same process must logically offer an improved means of obtaiing the alpha-mono-substituted (3-thienyl)-acetic acids. As will be shown further on in detail, the process forming one of the objects of the invention does, in fact, provide a means of obtaining the nitriles in question which is very simple and consequently markedly superior to what is known up to present. Furthermore, the process forming one of the objects of the invention enables alpha,alpha-di-substituted nitriles to be obtained with the same ease as those bearing only one substituent in alpha.

Such alpha,alpha-di-substituted (3-thienyl)-acetonitriles are described in U.S. Pat. No. 2,685,589 as intermediate products for the direct preparation of the corresponding esters. The latter are recognized as possessing valuable pharmacological properties in that they exhibit an antispasmodic action more particularly an antispasmodic action on normal smooth muscle as well as against neurotropic and musculotropic spasms of smooth muscle. They are also useful as antifungal agents.

Other alpha,alpha-di-substituted (3-thienyl)-acetic esters which may be prepared from the compounds of Formula I are disclosed in French Pat. No. 2.150.716

(B) [72 27660]—Aug. 1, 1972, as possessing useful antiphlogistic and antiarthritic properties.

However, the methods known up to present for the preparation of these alpha,alpha-di-substituted thienyl-acetonitriles, such as the process described in U.S. Pat. No. 2,685,589, a process which could also be used for preparing the mono-substituted derivatives as well, would be very difficult to employ on the industrial scale.

According to this process, the alpha,alpha-di-substituted thienyl-acetonitriles in question are obtained by reacting the corresponding thienyl-acetonitrile at a temperature of −50° C in liquid ammonia to which sodium has been added with what is termed in the said U.S. Pat. No. 2,685,289 as pentamethylene and tetramethylene bromides.

The use of this process on the industrial scale presents several disadvantages of which the principal ones may be summarized as follows:

(a) The use of liquid ammonia raises practical problems since it is necessary to operate at low temperatures (usually about −50° C) on the industrial scale. The employment of this substance imposes the need for special refrigerating equipment and means for recycling the ammonia lost by evaporation, which presupposes a considerable financial outlay.

(b) The use of liquid ammonia and sodium for preparing the alpha-sodium derivative of a thienyl-acetonitrile is equivalent to employing sodium amide as the source of sodium which can be dangerous to handle after elimination of the ammonia as sodium amide is obtained in powdery form. The handling of this powdery sodium amide raises a problem of safety because, in solid state, it often causes violent explosions.

The process forming one of the objects of the invention enables these disadvantages to be avoided.

According to the invention, it has in fact been found that a temperature of −50° C is not at all essential for replacing an alkali metal in position alpha of a thienyl-acetonitrile by a halide and that this reaction may be carried out at temperature above −50° C which offers the following advantages:

(i) The temperatures employed in the process of the invention which are in the range of −20° to +80° C, are more accessible than a temperature of −50° C, thus simplifying the application of the process on the industrial scale (elimination, for example, of the need for a refrigerating chamber).

(ii) It is possible to eliminate the liquid ammonia which can be replaced by solvents which are readily available and in common use. To carry out the process of the invention, it is sufficient to use an inert medium which is in liquid form at the reaction temperatures employed, i.e. from −20° to +80° C which is suitable for a very wide range of solvents.

(iii) The agents constituting a source of alkali metal which are used in the presence of the invention for preparing the metallic derivatives of (3-thienyl)-acetonitrile and which include sodium amide, are employed in a manner which does not involve the danger of explosion.

In the light of the advantages described above, the process of the invention is more rewarding than that described in U.S. Pat. No. 2,685,589 since it presents less difficulties to be overcome. Thus, the process of the invention makes it possible to obtain easily and with good yield the nitriles of formula I whether the latter be mono- or di-substituted in alpha.

Here again, the fact that the process of preparing alpha-substituted or alpha,alpha-di-substituted thienyl-acetonitriles in accordance with the present invention is superior to that described in U.S. Pat. No. 2,685,589 means that the present invention automatically offers an improved method of obtaining the pharmacologically useful esters described in the said U.S. patent.

Thus, it may be concluded that the acetonitriles prepared in accordance with the process forming one of the objects of the invention constitute, by virtue of the ease with which they are prepared, particularly useful intermediate products for obtaining the pharmacologically valuable thiophene derivatives mentioned above.

According to the process of the invention, the compounds of formula I are prepared by treating at a temperature between −20° and +80° C a reaction medium comprising a solvent such as, for example, dimethylformamide, benzene, toluene, xylene, dimethylsulfoxide or hexamethylphosphotriamide, and a compound of the general formula:

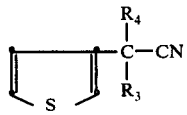

II wherein $R_3$ represents an atom of alkali metal, preferably sodium, and $R_4$ represents an atom of hydrogen or of alkali metal, such as sodium, or the radical methyl, with the appropriate quantity of a halide of the general formula:

$$R_5X \qquad\qquad III$$

in which X represents an atom of fluorine, chlorine, bromine or iodine and $R_5$ represents an alkyl radical containing 1 to 4 carbon atoms, a cycloalkyl, cycloalkenyl or aralkyl radical or the group —$CH_2(CH_2)_nX$ in which n is an integer in the range of from 1 to 4 inclusive and X has the meaning given above with the proviso that when $R_4$ represents methyl $R_5$ represents alkyl, and when $R_3$ and $R_4$ both represent an atom of alkali metal $R_5$ represents the group —$CH_2(CH_2)_nX$.

Treatment is carried out preferably at a temperature between −20° and +30° C according to the reagents employed.

In accordance with known chemical procedures and when it is desired to place two identical substituents in positions alpha,alpha of the compounds of formula II, the compound of formula II is treated so that at least two molar equivalents of the halide of formula III, preferably in excess, react with one molar equivalent of the compound of formula II. When it is desired to place one single substituent in position alpha of the compounds of formula II, the compound of formula II is treated so that one molar equivalent of the halide of formula III reacts with one molar equivalent of the compound of formula II. This latter proportion is also observed when it is desired to attach a cyclopolymethylene radical in positions alpha,alpha of the compound of formula II.

The compounds of formula II may be obtained by reacting at room temperature or by heating in an appropriate medium such as, for example, dimethylformamide, benzene, toluene, xylene, dimethylsulfoxide or hexamethylphosphotriamide, a nitrile of the general formula:

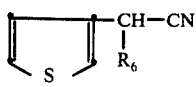

wherein $R_6$ represents an atom of hydrogen or a methyl radical, with the appropriate quantity of an agent capable of supplying an atom of alkali metal, the said agent being designated hereinafter by the symbol M which corresponds to sodium, potassium or lithium or to the amide or hydride of these alkali metals, to obtain the corresponding derivative of formula II.

In accordance with known chemical procedures, the quantity of M is calculated so that 1 or 2 molar equivalents of M react with one molar equivalent of the compound of formula IV.

The compound of formula IV in which $R_6$ represents a methyl radical is in fact that compound of formula I in which $R_2$ represents hydrogen and $R_1$ is an alkyl radical containing 1 atom of carbon.

The nitrile of formula IV in which $R_6$ represents hydrogen i.e. (3-thienyl)-acetonitrile is a known compound.

The process described above for the preparation of (3-thienyl)-acetonitriles substituted in alpha can be carried out in accordance with several different procedures. These different procedures are, however, only simple variations which in no way go outside of the limits of the process claimed herein and may be selected according to the preference of the operator. These variations are composed essentially of the following:

(i) First attach the alkali metal in position $\alpha$ of the compound of formula IV by reaction with the appropriate quantity of M then add to the compound of formula II thus obtained the appropriate quantity of the halide of formula III.

(ii) Add a suitable molecular mixture of a halide of formula III and a nitrile of formula IV directly to a suspension of, for example, sodium or sodium hydride in the solvent required to ensure the desired reaction.

(iii) Add a suspension of, for example, sodium amide also in the solvent required to ensure the desired reaction, to a suitable molecular mixture of a nitrile of formula IV and a halide of formula III.

In the last two variations, there is the intermediate formation of the corresponding compound of formula II in the presence of the halide of formula III.

The process forming one of the objects of the invention offers, as stated above, not only the possiblity of avoiding the disadvantages characterizing the methods already known but also presents certain valuable advantages on the practical plane.

Through the process of the invention, the operator can utilize reagents which are readily obtainable on the market or relatively easy to prepare, often at moderate prices, such as the halides of formula III and the reagent M which supplies the alkali metal.

In addition, the process of the invention does not make it necessary to maintain the reactions at very low temperatures, which serves to eliminate a number of problems inherent in this type of procedure, nor does it impose the use of dangerous solvents such as the ethers.

The process forming one of the objects of the invention is illustrated by the following non-limitative Examples:

EXAMPLE 1

Preparation of α-(3-thienyl)-α-cyclohexyl-acetonitrile

In a 100 ml-flask fitted with a mechanical stirrer, a vertical condensor protected by a calcium chloride stopper, a dropping-funnel and a source of nitrogen were introduced 30 ml of hexamethylenephosphotriamide and 2.3 g (0.1 mol) of finely cut sodium wire. A mixture of 12.3 g (0.1 mol) of (3-thienyl)-acetonitrile and 16.3 g (0.1 mol) of cyclohexyl bromide was then quickly added at a temperature of 20° C. The reaction mixture was then maintained under nitrogen atmosphere and stirred for 12 hours at room-temperature. The excess of sodium was destroyed by adding 5 ml of ethanol and the organic solution was slowly poured into 100 ml of a 1N iced solution of hydrochloric acid. The solution was extracted twice with 100 ml ether. The ethereal phases were collected, washed with water, dried and concentrated under reduced pressure. The crude product was then purified by chromatography on a silica column (150 g of silica) using a 1/1 benzene/cyclohexane mixture as elution agent. The product obtained was rectified by distillation.

In this manner, 3.4 g of α-(3-thienyl)-α-cyclohexyl-acetonitrile were obtained, which represents a yield of 16%.

B.P. 130° C under 3 mm Hg.

EXAMPLE 2

Preparation of α-(3-thienyl)-α-cyclohexyl-acetonitrile

In a flask fitted as in Example 1 hereabove, were placed 350 ml of anhydrous benzene, 86 g (0.7 mol) of (3-thienyl)-acetonitrile and 114 g (0.7 mol) of cyclohexyl bromide. Under nitrogen atmosphere, a suspension of 27 g of sodium amide in 250 ml of anhydrous benzene were added to the mixture. The reaction was exothermic and, for this reason, the sodium amide was introduced into the reaction medium slowly so that the temperature was maintained between 20° and 25° C. After this operation, the reaction medium was stirred for three hours at room-temperature. Then, 50 ml of ethanol were added and the solution was slowly poured into 1 liter of a 1N solution of hydrochloric acid. The benzene phase was decanted and the aqueous phase was extracted with 500 ml of ether. The organic phases were collected, washed with water, dried and concentrated under reduced pressure. The crude product was then purified by chromatography on a column of silica (800 g of silica) using a 1/1 benzene/cyclohexane mixture as elution agent.

In this manner, 75 g of α-(3-thienyl)-α-cyclohexyl-acetonitrile were obtained, which represents a yield of 52%.

$n_D^{20} = 1.5390$.

EXAMPLE 3

Preparation of α-(3-thienyl)-α-cyclohexyl-acetonitrile

In a 100 ml-flask fitted as in Example 1 hereabove, were placed 45 ml of dimethylformamide and 4 g (0.165 mol) of a suspension of sodium hydride in oil. The reaction mixture was cooled to −20° C by means of a bath comprising acetone and carbon dioxide ice and, then a mixture of 27 g (0.165 mol) of cyclohexyl bromide and 20 g (0.15 mol) of (3-thienyl)-acetonitrile was slowly added under nitrogen atmosphere.

The reaction was strongly exothermic and the medium was maintained at a temperature of $-20°$ C. Stirring was continued for two hours at $-20°$ C, after which the temperature was allowed to return slowly to room-temperature, the mixture being stirred and maintained under nitrogen atmosphere all the time.

The reaction was allowed to continue for 12 hours at $+20°$ C and then the mixture was poured into 150 ml of a 1N iced solution of hydrochloric acid. The aqueous solution was extracted twice with 100 ml of ether, the ethereal phases were collected, washed with water, dried and concentrated under reduced pressure. The crude product so obtained was then distilled.

In this manner, 16 g of α-(3-thienyl)-α-cyclohexyl-acetonitrile were obtained, which represents a yield of 50%.

B.P. 130°–135° C under 3 mm Hg.

Following the same procedure as that described above but using the appropriate starting-products the compound hereunder was prepared:

| Compound | Melting point in ° C |
|---|---|
| α-(3-thienyl)-α-benzyl-acetonitrile | 63–64 |

EXAMPLE 4

Preparation of alpha-(3-thienyl-alpha,alpha-cyclopentamethylene-acetonitrile

In a 100 ml-flask, fitted as in Example 1 hereabove, were introduced 50 ml of dimethylformamide and an oily suspension of 2.4 g (0.1 mol) of sodium hydride. The reaction mixture was cooled to $-10°$ C and a mixture of 6.1 g (0.05 mol) of (3-thienyl)-acetonitrile and 12 g (0.054 mol) of 1,5-dibromopentane was then added drop-by-drop. The operation was carried out in one hour, care being taken that the temperature of the mixture did not exceed $-10°$ C.

The reaction medium was then allowed to return to room temperature and stirring was maintained for 12 hours. The solution was then slowly poured into 60 ml of a 1N iced solution of hydrochloric acid.

The mixture was extracted twice with 100 ml of ether. The ethereal phases were collected, dried and concentrated under reduced pressure. The oil so obtained was then distilled.

In this manner, 3.1 g of alpha-(3-thienyl)-alpha,alpha-cyclopentamethylene-acetonitrile were obtained, which represents a yield of 35%.

B.P. 140°–142° C under 3 mm Hg.

EXAMPLE 5

Preparation of alpha-(3-thienyl)-alpha,alpha-cyclotetramethylene-acetonitrile

In a 250 ml-flask fitted as in Example 1 hereabove, were placed 4.5 g (0.2 mol) of sodium hydride and 70 ml (0.2 mol) of dimethylformamide. The reaction medium was cooled to $-15°$ C and then a mixture of 12.3 g (0.1 mol) of (3-thienyl)-acetonitrile and 22.4 g (0.11 mol) of 1,4-dibromo-butane was added drop-by-drop, care being taken that the temperature did not exceed $-10°$ C. This operation was effected in about 45 minutes. The reaction medium was then allowed to return slowly to room temperature and stirring was maintained for 12 hours. The solution was then slowly poured into 100 ml of a 1N iced solution of hydrochloric acid. The mixture was extracted three times with 100 ml of ether. The ethereal phases were collected, dried and then concentrated under reduced pressure. The crude product so obtained was then purified by distillation.

In this manner, 11 g of alpha-(3-thienyl)-alpha,alpha-cyclotetramethylene-acetonitrile were obtained, which represents a yield of 56%.

B.P. 122° C under 3 mm Hg.

We claim:

1. A novel thiophene derivative corresponding to the general formula:

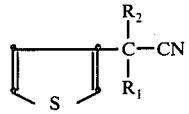

Ia wherein $R_1$ represents a cyclohexyl radical and $R_2$ represents a hydrogen atom.

* * * * *

UNITED STATES PATENT OFFICE
CERTIFICATE OF CORRECTION

Patent No. 4,108,865     Dated August 22, 1978

Inventor(s) Charles Pigerol, et al.

It is certified that error appears in the above-identified patent and that said Letters Patent are hereby corrected as shown below:

First page, first column, below item [22], the following is inserted:

--[30] Foreign Application Priority Data
August 30, 1973 [FR] France 73 31322--.

Signed and Sealed this

Thirtieth Day of October 1979

[SEAL]

Attest:

RUTH C. MASON
Attesting Officer

LUTRELLE F. PARKER
Acting Commissioner of Patents and Trademarks